United States Patent
Eberler et al.

(10) Patent No.: US 8,064,981 B2
(45) Date of Patent: Nov. 22, 2011

(54) DEVICE FOR SUPERIMPOSED MRI AND PET IMAGING

(75) Inventors: Ludwig Eberler, Postbauer-Heng (DE); Razvan Lazar, Erlangen (DE); Jürgen Nistler, Erlangen (DE); Wolfgang Renz, Erlangen (DE); Norbert Rietsch, Dormitz (DE)

(73) Assignee: Siemens Aktiengesellschaft, Munich (DE)

(*) Notice: Subject to any disclaimer, the term of this patent is extended or adjusted under 35 U.S.C. 154(b) by 869 days.

(21) Appl. No.: 11/984,479

(22) Filed: Nov. 19, 2007

(65) Prior Publication Data
US 2008/0139924 A1 Jun. 12, 2008

(30) Foreign Application Priority Data
Nov. 20, 2006 (DE) .................. 10 2006 054 542

(51) Int. Cl.
*A61B 5/05* (2006.01)
(52) U.S. Cl. .................. 600/407; 600/410; 600/411
(58) Field of Classification Search .................. 600/407, 600/410, 411, 425, 427; 250/363.02, 363.03, 250/363.04, 363.05, 363.08
See application file for complete search history.

(56) References Cited

U.S. PATENT DOCUMENTS

| | | | | |
|---|---|---|---|---|
| 4,939,464 A * | 7/1990 | Hammer | .................. | 324/318 |
| 5,303,707 A * | 4/1994 | Young | .................. | 600/423 |
| 5,773,829 A * | 6/1998 | Iwanczyk et al. | .................. | 250/367 |
| 6,060,883 A * | 5/2000 | Knuttel | .................. | 324/318 |
| 6,490,476 B1 * | 12/2002 | Townsend et al. | .................. | 600/427 |
| 6,754,519 B1 * | 6/2004 | Hefetz et al. | .................. | 600/407 |
| 6,754,520 B2 * | 6/2004 | DeSilets et al. | .................. | 600/415 |
| 6,925,319 B2 * | 8/2005 | McKinnon | .................. | 600/407 |
| 6,941,164 B2 * | 9/2005 | Hajaj et al. | .................. | 600/407 |
| 6,946,841 B2 * | 9/2005 | Rubashov | .................. | 324/318 |
| 6,961,606 B2 * | 11/2005 | DeSilets et al. | .................. | 600/415 |
| 7,102,135 B2 * | 9/2006 | Lecoq | .................. | 250/363.03 |
| 7,218,112 B2 * | 5/2007 | Ladebeck et al. | .................. | 324/318 |
| 7,254,438 B2 * | 8/2007 | DeSilets et al. | .................. | 600/427 |
| 7,286,867 B2 * | 10/2007 | Schlyer et al. | .................. | 600/407 |
| 7,323,874 B2 * | 1/2008 | Krieg et al. | .................. | 324/318 |
| 7,394,254 B2 * | 7/2008 | Rieke et al. | .................. | 324/318 |
| 7,522,952 B2 * | 4/2009 | Krieg et al. | .................. | 600/411 |
| 7,603,165 B2 * | 10/2009 | Townsend et al. | .................. | 600/427 |
| 7,626,389 B2 * | 12/2009 | Fiedler et al. | .................. | 324/309 |
| 7,667,457 B2 * | 2/2010 | Linz et al. | .................. | 324/307 |
| 7,719,277 B2 * | 5/2010 | Eberler et al. | .................. | 324/318 |
| 7,723,694 B2 * | 5/2010 | Frach et al. | .................. | 250/370.11 |
| 7,745,794 B2 * | 6/2010 | Schmidt | .................. | 250/363.03 |

(Continued)

OTHER PUBLICATIONS

Shao et al, "Development of a PET Detector System Compatible with MRI/NMR Systems" IEEE Transactions on Nuclear Science vol. 44 No. 3 Jun. 1997 pp. 1167-1171.*

(Continued)

*Primary Examiner* — Francis Jaworski
(74) *Attorney, Agent, or Firm* — Harness, Dickey & Pierce, P.L.C.

(57) ABSTRACT

A device for superposed magnetic resonance tomography and positron emission tomography imaging is disclosed. In at least one embodiment, the device includes a magnetic resonance tomography magnet, which defines a longitudinal axis; a magnetic resonance tomography gradient coil, arranged radially within the magnetic resonance tomography magnet; a magnetic resonance tomography RF coil, arranged radially within the magnetic resonance tomography gradient coil; and a multiplicity of positron emission tomography detection units, arranged in pairs lying opposite to one another about the longitudinal axis. In at least one embodiment, the many positron emission tomography detection units are arranged radially within the magnetic resonance tomography gradient coil and are arranged along the longitudinal axis next to the magnetic resonance tomography RF coil.

17 Claims, 2 Drawing Sheets

U.S. PATENT DOCUMENTS

| | | | |
|---|---|---|---|
| 7,822,459 B2* | 10/2010 | Cho et al. | 600/407 |
| 7,827,635 B2* | 11/2010 | Wang et al. | 5/601 |
| 7,835,782 B2* | 11/2010 | Cherry et al. | 600/411 |
| 7,847,552 B2* | 12/2010 | Haworth et al. | 324/318 |
| 2003/0212320 A1* | 11/2003 | Wilk et al. | 600/407 |
| 2006/0052685 A1* | 3/2006 | Cho et al. | 600/407 |
| 2007/0081703 A1* | 4/2007 | Johnson | 382/128 |
| 2007/0102641 A1* | 5/2007 | Schmand et al. | 250/363.03 |
| 2008/0008401 A1* | 1/2008 | Zhu et al. | 382/294 |
| 2008/0137930 A1* | 6/2008 | Rosen | 382/131 |
| 2008/0146914 A1* | 6/2008 | Polzin et al. | 600/420 |
| 2008/0214927 A1* | 9/2008 | Cherry et al. | 600/411 |
| 2010/0106004 A1* | 4/2010 | Harvey | 600/411 |

OTHER PUBLICATIONS

D. Schlyer et al. "Development of a Simultaneous PET/MRI Scanner", Nuclear Science Symposium Conference Record 2004, 16.-22.10.2004, vol. 4, 3419-3421.

Markus Schwaiger et al.; MR-PET: Combining Function, Anatomy, and More Medical Solutions/Special Molecular Imaging, Siemens AG, Sep. 2005,; Others; S. 25-30.

J. Carstens "PET Einschub für Kernspintomograph" IN: Ipcom Nr.: IPCOM000099118D, Apr. 16, 2005: Others.

German Office Action.

* cited by examiner

DEVICE FOR SUPERIMPOSED MRI AND PET IMAGING

PRIORITY STATEMENT

The present application hereby claims priority under 35 U.S.C. §119 on German patent application number DE 10 2006 054 542.7 filed Nov. 20, 2006, the entire contents of which is hereby incorporated herein by reference.

FIELD

Embodiments of the present invention generally relate to a device for superimposed MRI and PET imaging.

BACKGROUND

It is known that a magnetic resonance tomography machine (MRI machine) comprises, amongst others, those three functional modules which are illustrated in FIG. 2: a basic field system 11, a gradient system 12, and a radiofrequency system 13 (also called a RF-system or body resonator). The basic field system 11 is generally a magnet and provides a strong, static magnetic field. The gradient system 12 provides an adjustable magnetic field in the low frequency region up to approximately 1 kHz, which has a linearly increasing or decreasing course in one or a number of directions. In the radiofrequency region, the RF-system 13 provides, in the vicinity of the nuclear magnetic resonance frequency essentially given by the static magnetic field (in general, 42.45 MHz), an oscillating magnetic field for the excursion of the nuclear spins, which can furthermore also serve to receive the signals of the relaxing nuclear spins.

These three modules are arranged in conventional magnetic resonance tomography machines around the patient to be examined in the following order, arranged in a radial direction from the inside outwards: RF-system 13, gradient system 12 and basic field system 11. The patient lies on a couch 14, which is located radially within the RF-system 13.

Alongside magnetic resonance tomography (MRI) positron emission tomography (PET) has also become increasingly widespread of recent years in medical diagnosis. While MRI is an imaging method for displaying structures and slice images in the interior of the body, PET enables the visualization and quantification of metabolic activities in vivo.

PET uses the particular properties of positron emitters and positron annihilation in order to determine the function of organs or cell areas quantitatively. In this case, before the examination the patient is administered appropriate radiopharmaceuticals that are marked with radionuclides. In the event of decay, the radionuclides emit positrons that interact with an electron after a short distance, resulting in a so-called annihilation. Two gamma quanta are produced in this case and fly apart from one another in opposite directions (offset by 180°). The gamma quanta are detected by two opposite PET detector modules inside a specific time window (coincidence measurement), as a result of which the location of annihilation is determined at a position on the connecting line between these two detector modules.

For detection, the PET-detector modules are arranged around the patient in an annular fashion and generally cover a major part of the length of the gantry arc. When detecting a gamma quantum, each PET-detector module generates an event record that specifies the time and the detection location, that is to say the appropriate detector element. These items of information are transferred to a fast logic unit and compared.

If two events coincide within a maximum time spacing, it is assumed there is a gamma decay process on the connecting line between the two associated PET-detector modules. The reconstruction of the PET image is performed with aid of a tomography algorithm, that is to say the so-called back projection.

A superimposed imaging of the two methods is desirable in many instances on the basis of the different items of information that are obtained by MRI and PET.

To combine the imaging MRI and PET methods in one machine, it is necessary to arrange inside the basic field system and the gradient system the two units of the RF system and the PET detectors required for the data acquisition. A concentric arrangement, in which the RF system would be positioned inside the annularly arranged PET detectors, would be associated with a number of difficulties.

First, the structure of the interior coil arrangement (transmitting and receiving coils) of the RF system reduces the sensitivity of the annularly arranged PET detectors, which requires a correction during the PET image reconstruction.

Also, nesting the RF system and the annularly arranged PET detectors from the inside to the outside greatly reduces the interior diameter remaining for the patient.

Moreover, the distance between the annularly arranged PET detectors and the RF conductor structures that is required for a high quality of the RF body resonator has to be greatly reduced (field return space).

Finally, due to the radial spatial conditions, it is not possible to screen the annularly arranged PET detectors (e.g. by septa) against gamma radiation from the outside of the annularly arranged PET detectors.

SUMMARY

In at least one embodiment, the present invention provides a device for superimposed MRI and PET imaging, which constricts the interior diameter of the patient tunnel less and yet can ensure screening and an excellent image quality.

According to at least one embodiment of the present invention, a device for superimposed magnetic resonance tomography and positron emission tomography imaging has a magnetic resonance tomography magnet, which defines a longitudinal axis; a magnetic resonance tomography gradient coil, which is arranged radially within the magnetic resonance tomography magnet; a magnetic resonance tomography RF coil, which is arranged radially within the magnetic resonance tomography gradient coil; and a multiplicity of positron emission tomography detection units, which are arranged in pairs lying opposite to one another about the longitudinal axis.

The many positron emission tomography detection units are arranged radially within the magnetic resonance tomography gradient coil. The many positron emission tomography detection units are arranged along the longitudinal axis next to the magnetic resonance tomography RF coil.

Preferably, the magnetic resonance tomography RF coil is arranged along the longitudinal axis centric to the magnetic resonance tomography magnet, so that the many positron emission tomography detection units are offset along the longitudinal axis from the middle of the magnetic resonance tomography magnet.

In at least one embodiment, this arrangement offers at least one of the following advantages:

The interior diameter of the patient tunnel is less constricted by this arrangement than in the concentric variation.

The magnetic resonance tomography RF coil and the many positron emission tomography detection units are decoupled from each other to a great extent and can be optimized better with regard to their image quality.

The attenuation of the gamma radiation by resonator structures lying within the many positron emission tomography detection units is eliminated.

Costly measures for the detection and correction of structures lying within the many positron emission tomography detection units (attenuation correction) are eliminated. This saves examination time and computing time during image reconstruction.

The radial interior space inside the positron emission tomography detection units is enlarged, thus enabling a larger FOV (field of view).

Preferably, the many positron emission tomography detection units are held together in such a way, that they form an annulus about the longitudinal axis, the magnetic resonance tomography RF coil and the annulus formed by the many positron emission tomography detection units essentially having the same width along the longitudinal axis.

Despite a geometric offset between the RF system and the annularly arranged positron emission tomography detection units, the arrangement allows a quasi parallel acquisition of MRI and PET images. That is to say, with a given position of a patient within the arrangement, MRI measurement is taking place in a first part of the volume, whilst the PET signals are being acquired in a second part of the volume at the same time. The time lost for an examination of the patient compared to the concentric arrangement corresponds to the measuring time for a so-called "bed position." Overall, the arrangement has a considerable speed advantage compared to serial measurement in the case of a patient in two separate machines, arranged one behind the other.

Finally, construction on a common carrier or carrier pipe is possible, resulting in economical production.

Preferably, the many positron emission tomography detection units are screened by septa. Due to the enabled, larger interior diameter of the annularly arranged positron emission tomography detection units screening against scattered rays (singles) is possible from the outer side of the PET annulus.

Preferably, the positron emission tomography detection units each have an avalanche photodiode array (APD; avalanche photodiode) with an upstream lutetium oxyorthosilicate crystal array (LSO) and an electrical amplifying circuit. The previous realization of PET detectors with PMTs (photo multipliers) did not allow for use inside an outer magnetic field. Only the availability of APDs as an amplifier element has favored the operation of a PET-detector within a basic field system.

BRIEF DESCRIPTION OF THE DRAWINGS

An example embodiment of the invention will now be described with reference to the attached drawings, in which.

Figure 1:
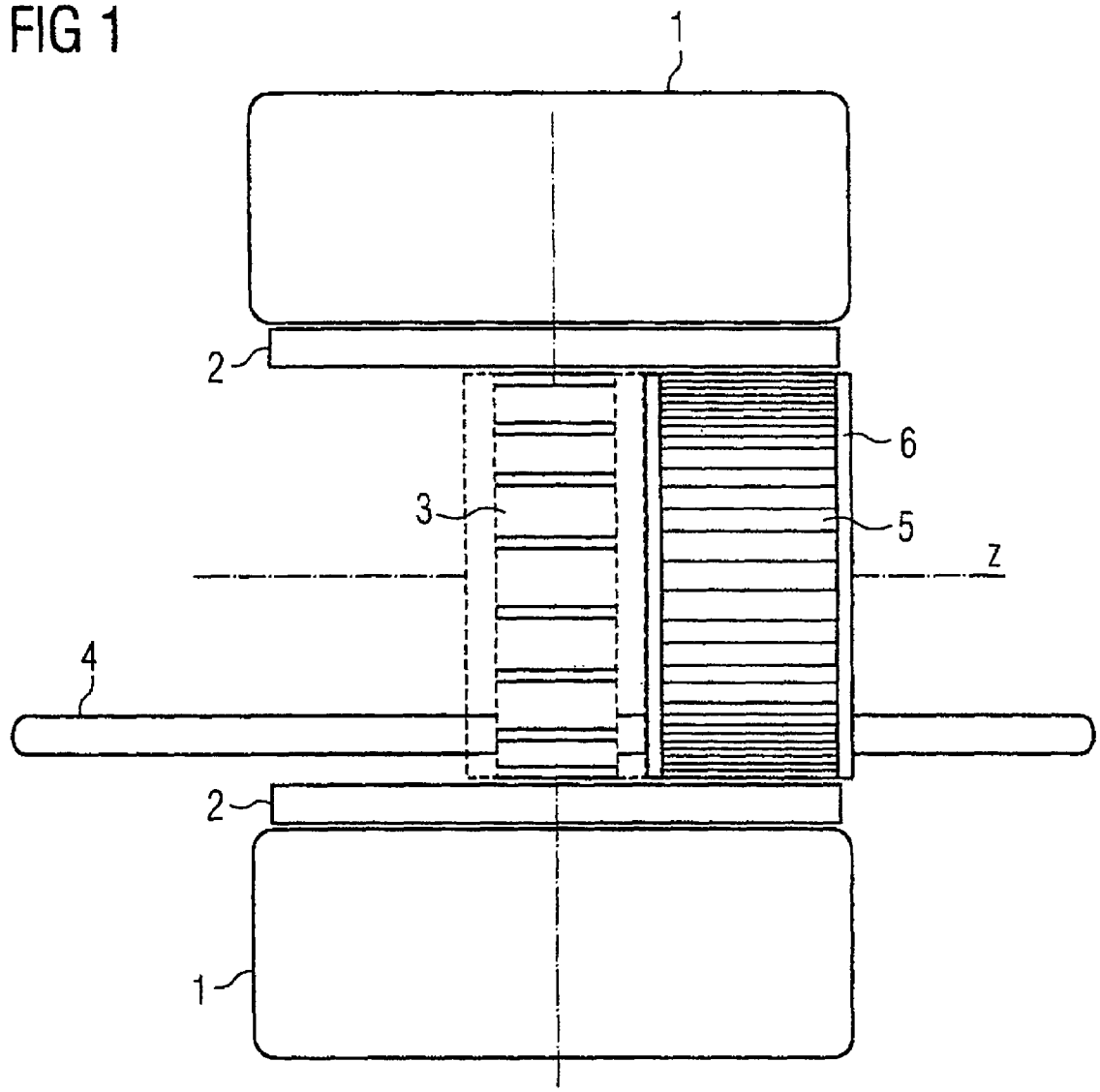
FIG. 1 shows a device for superposed magnetic resonance tomography and positron emission tomography imaging in accordance with an example embodiment of the present invention.
Figure 2:
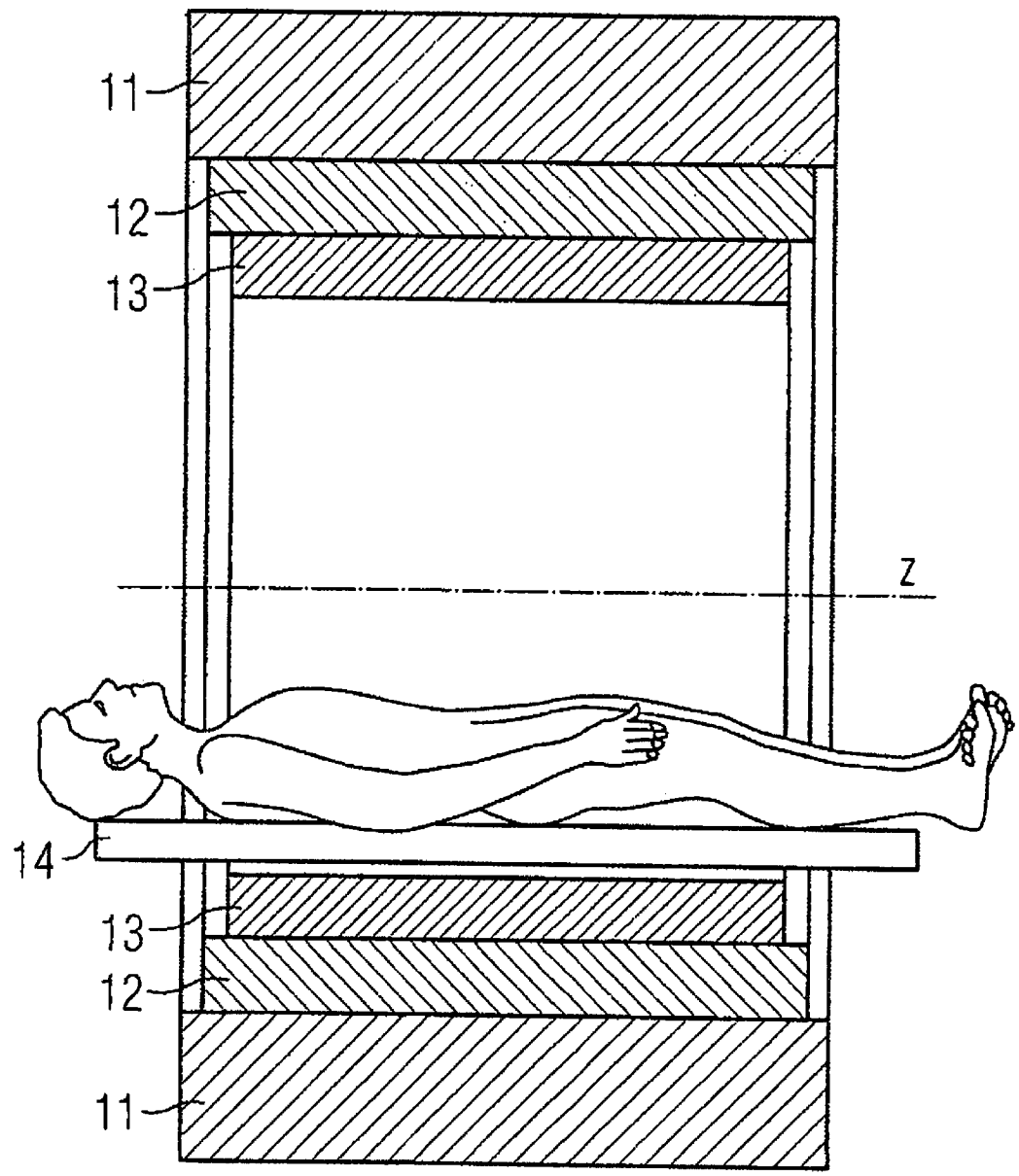
FIG. 2 shows a known device for magnetic resonance tomography imaging according to prior art.

The example embodiments of the present invention are described below with reference to the drawings.

DETAILED DESCRIPTION OF THE EXAMPLE EMBODIMENTS

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described. Like numbers refer to like elements throughout. As used herein, the terms "and/or" and "at least one of" include any and all combinations of one or more of the associated listed items.

FIG. 1 shows a device for superposed magnetic resonance tomography and positron emission tomography imaging in accordance with the example embodiment of the present invention.

In accordance with an embodiment of the present invention, the device for superposed magnetic resonance tomography and positron emission tomography imaging comprises a magnetic resonance tomography magnet 1, which defines a longitudinal axis z. The magnetic resonance tomography magnet 1 forms a basic field system, which provides a strong static magnetic field.

Furthermore, the device comprises a magnetic resonance tomography gradient coil 2, which is arranged radially within the magnetic resonance tomography magnet 1 and preferably coaxially with the longitudinal axis z. The magnetic resonance tomography gradient coil 2 forms a gradient system, which provides an adjustable magnetic field in the low frequency region.

The device further comprises a magnetic resonance tomography RF coil 3, which is arranged radially within the magnetic resonance tomography gradient coil 2 and preferably coaxially with the longitudinal axis z. The magnetic resonance tomography RF coil 3 forms an RF system, which provides, in the radiofrequency region, in the vicinity of the nuclear magnetic resonance frequency essentially given by the static magnetic field (in general, 42.45 MHz), an oscillating magnetic field for the excursion of the nuclear spins. The magnetic resonance tomography RF coil 3 can furthermore also serve to receive signals of the relaxing nuclear spins.

A couch 4 is provided for the patient.

Furthermore, the device has a multiplicity of positron emission tomography detection units 5, which are arranged in pairs lying opposite to one another about the longitudinal axis z.

The many positron emission tomography detection units 5 are arranged radially within the magnetic resonance tomography gradient coil 2 and preferably coaxially with the longitudinal axis z. The many positron emission tomography detection units 5 are arranged along the longitudinal axis z next to the magnetic resonance tomography RF coil 3.

The magnetic resonance tomography RF coil 3 is arranged along the longitudinal axis z centric to the magnetic resonance tomography magnet 1, so that the many positron emission tomography detection units 5 are offset along the longitudinal axis z from the middle of the magnetic resonance tomography magnet 1.

Overall, this leads to an arrangement, in which the magnetic resonance tomography magnet 1, the magnetic resonance tomography gradient coil 2 and the magnetic resonance tomography RF coil 3 are aligned centrically with respect to one another along the longitudinal axis z, and only the many positron emission tomography detection units 5 are offset to one side from the middle of the magnetic resonance tomography magnet 1 along the longitudinal axis z.

It is furthermore clear from FIG. 1, that the magnetic resonance tomography magnet 1 and the magnetic resonance tomography gradient coil 2 both have an extent along the longitudinal axis z, which coves both the positron emission tomography detection units 5 and the magnetic resonance tomography RF coil 3.

Thus space is saved in the device in the radial direction, which leads to the advantages listed in the introduction of the description.

In the example embodiment shown, the many positron emission tomography detection units 5 are held together in such a way that they form an annulus about the longitudinal axis z. This annulus essentially has the same width along the longitudinal axis z as the magnetic resonance tomography RF coil 3. The width of the magnetic resonance tomography RF coil 3 is here of the order of, for example, 30 cm. Altogether, this leads to a total length of the arrangement of approximately 60-70 cm (depending on the required separation between the components).

In the example embodiment shown, the many positron emission tomography detection units 5 are screened by septa 6.

The positron emission tomography detection units 5 each comprise an avalanche photodiode array with an upstream lutetium oxyorthosilicate crystal array and an electrical amplifying circuit, which enables the compact design of the positron emission tomography detection units 5. However, the embodiments of the invention is not restricted to exclusively using the avalanche photodiode array with an upstream lutetium oxyorthosilicate crystal array and the electrical amplifying circuit. Differently designed, compact positron emission tomography detection units can be used as well.

Alternatively, an apparatus can be provided, which moves the positron emission tomography detection units 5 and/or the magnetic resonance tomography RF coil 3 along the longitudinal axis z within the magnetic resonance tomography gradient coil 2.

The invention is not restricted by the disclosed example embodiments, but there is a possibility of modifications and equivalent embodiments within the scope of the invention that is defined by the claims.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A device for superposed magnetic resonance tomography and positron emission tomography imaging comprising:
   a magnetic resonance tomography magnet, which defines a longitudinal axis (z);
   a magnetic resonance tomography gradient coil, arranged radially within the magnetic resonance tomography magnet;
   a magnetic resonance tomography RF coil, arranged radially within the magnetic resonance tomography gradient coil;
   a multiplicity of positron emission tomography detection units, arranged in pairs lying opposite to one another about the longitudinal axis, the multiplicity of positron emission tomography detection units being arranged radially within the magnetic resonance tomography gradient coil and the multiplicity of positron emission tomography detection units being arranged along the longitudinal axis next to the magnetic resonance tomography RF coil, wherein in the direction of the longitudinal axis the multiplicity of positron emission tomography detection units and the magnetic resonance tomography RF coil are arranged side by side.

2. The device as claimed in claim 1, wherein the magnetic resonance tomography RF coil is arranged along the longitudinal axis centric to the magnetic resonance tomography magnet, so that the multiplicity of positron emission tomography detection units are offset along the longitudinal axis from the middle of the magnetic resonance tomography magnet.

3. The device as claimed in claim 2, wherein the multiplicity of positron emission tomography detection units are held together in such a way that they form an annulus about the longitudinal axis.

4. The device as claimed in claim 3, wherein the magnetic resonance tomography RF coil and the annulus formed from the multiplicity of positron emission tomography detection units essentially has the same width along the longitudinal axis.

5. The device as claimed in claim 4, wherein the multiplicity of positron emission tomography detection units are screened by septa.

6. The device as claimed in claim 5, wherein the positron emission tomography detection units each have an avalanche photodiode array with an upstream lutetium oxyorthosilicate crystal array and an electrical amplifying circuit.

7. The device as claimed in claim 3, wherein the multiplicity of positron emission tomography detection units are screened by septa.

8. The device as claimed in claim 2, wherein
the multiplicity of positron emission tomography detection units are screened by septa.

9. The device as claimed in claim 2, wherein
the positron emission tomography detection units each have an avalanche photodiode array with an upstream lutetium oxyorthosilicate crystal array and an electrical amplifying circuit.

10. The device as claimed in claim 1, wherein
the multiplicity of positron emission tomography detection units are held together in such a way that they form an annulus about the longitudinal axis.

11. The device as claimed in claim 10, wherein
the magnetic resonance tomography RF coil and the annulus formed from the multiplicity of positron emission tomography detection units essentially has the same width along the longitudinal axis.

12. The device as claimed in claim 11, wherein
the multiplicity of positron emission tomography detection units are screened by septa.

13. The device as claimed in claim 11, wherein
the positron emission tomography detection units each have an avalanche photodiode array with an upstream lutetium oxyorthosilicate crystal array and an electrical amplifying circuit.

14. The device as claimed in claim 10, wherein
the multiplicity of positron emission tomography detection units are screened by septa.

15. The device as claimed in claim 10, wherein
the positron emission tomography detection units each have an avalanche photodiode array with an upstream lutetium oxyorthosilicate crystal array and an electrical amplifying circuit.

16. The device as claimed in claim 1, wherein
the multiplicity of positron emission tomography detection units are screened by septa.

17. The device as claimed in claim 1, wherein
the positron emission tomography detection units each have an avalanche photodiode array with an upstream lutetium oxyorthosilicate crystal array and an electrical amplifying circuit.

* * * * *